United States Patent [19]

Bannai et al.

[11] Patent Number: 4,580,981
[45] Date of Patent: Apr. 8, 1986

[54] FLUORINE-CONTAINING MONOMER AND PROCESS FOR PRODUCING THE SAME

[75] Inventors: Nobuo Bannai; Hideyuki Yasumi; Shyoei Hirayama, all of Iwaki, Japan

[73] Assignee: Kureha Kagaku Kogyo Kabushiki Kaisha, Tokyo, Japan

[21] Appl. No.: 694,665

[22] Filed: Jan. 24, 1985

Related U.S. Application Data

[63] Continuation-in-part of Ser. No. 562,064, Dec. 16, 1983, abandoned.

[30] Foreign Application Priority Data

Dec. 24, 1982 [JP] Japan .................................. 57-233695

[51] Int. Cl.$^4$ ........................ A61K 6/08; A61C 13/02
[52] U.S. Cl. ............................ 433/168.1; 260/998.11; 433/180; 433/199.1; 523/120
[58] Field of Search ................ 523/120; 433/168, 180, 433/199; 526/250, 254, 255; 260/998.11

[56] References Cited

U.S. PATENT DOCUMENTS

| | | | |
|---|---|---|---|
| 3,073,795 | 1/1963 | Veverka | 523/120 |
| 3,457,247 | 7/1969 | Katsushima et al. | 560/223 |
| 3,483,263 | 12/1969 | Schlichting et al. | 568/843 |
| 3,523,133 | 8/1970 | Mailey et al. | 560/223 |
| 3,547,861 | 12/1970 | Anello et al. | 560/223 |
| 3,647,887 | 3/1972 | Anello et al. | 568/842 |

*Primary Examiner*—Lorenzo B. Hayes
*Attorney, Agent, or Firm*—Oblon, Fisher, Spivak, McClelland & Maier

[57] ABSTRACT

Disclosed herein is a novel fluorine-containing monomer having one carbon-carbon double bond at one of the main molecular chain ends thereof and a molecular weight of 300 to 1600, obtained by bringing a fluorine-containing telomer having a molecular weight of 200 to 1500 and an OH group at one of the main molecular chain ends thereof into esterification with acryloyl chloride or methacryloyl chloride.

7 Claims, No Drawings

FLUORINE-CONTAINING MONOMER AND PROCESS FOR PRODUCING THE SAME

CROSS-REFERENCE TO RELATED APPLICATION

The present application is a continuation-in-part of U.S. patent application Ser. No. 562,064, filed on Dec. 16, 1983 now abandoned.

BACKGROUND OF THE INVENTION

The present invention relates to a novel fluorine-containing, polymerizable monomer having a carbon-carbon double bond (hereinafter referred to as "a double bond") at one of its main molecular chain ends (hereinafter referred to as "the molecular chain ends") and a process for producing thereof. More in detail, the present invention relates to a novel fluorine-containing monomer having a double bond at one of its molecular chain ends and molecular weight of 300 to 1600, prepared by bringing a fluorine-containing telomer having a molecular weight of 200 to 1500 and an OH group at one of its molecular chain ends into esterification with acryloyl chloride or methacryloyl chloride.

Hitherto, there have been known numerous fluorine-containing, polymerizable monomers, and the polymers obtained from such a monomer have been broadly utilized as industrial material, materials for apparatus and instruments used in medical treatment and in electronics and the necessaries of life.

The present inventors have studied the utilization of fluorine-containing polymers comprising polyvinylidene fluoride for years as a material for apparatus and instruments used in medical treatment. For instance, although we have proposed a soft lining material for the denture base (refer to U.K. Patent Application GB No. 2027043A). U.K. Patent Application GB No. 2027043A discloses the soft lining material for lining the surface of the hard dental plate made of polymethyl methacrylate, which is contacted to the mucous membrane, with the soft fluoropolymer.

The demanded properties as a soft lining material for the dental plate are modulus of rigidity of 5 to 150 kg/cm$^2$, water absorbance of less than 0.7%, adhesion strength of more than 250 kg/cm$^2$, excellent compatibility to the mucous membrane, stability, etc. The lining material of the fluorine-containing polymer shows excellent properties as a soft lining material for the dental plate as compared with other lining material such as polyvinyl chloride, silicone rubber, etc. and accordingly the fluorine-containing polymer is extremely useful as a lining material for the dental plate.

However, since the operation of such a fluorine-containing polymer for equipping such a dental plate is not good, an improvement has been still demanded. In order to use the fluoropolymer of a high molecular weight as a surface material of the dental plate, which is contacted to the mucous membrane, it was found necessary to soften the fluoropolymer of a high molecular weight temporarily and thereafter to harden thereof again. The object of the present invention is to provide a novel fluorine-containing monomer solving the above-mentioned problems.

SUMMARY OF THE INVENTION

In the first aspect of the present invention, there is provided a novel fluorine-containing polymerizable monomer having a molecular weight of 300 to 1600 and a double bond at one of the molecular chain ends thereof, prepared by subjecting a mixture of not less than 50% by weight of vinylidene fluoride and at least one compound selected from the group consisting of vinyl fluoride, trifluoroethylene, tetrafluoroethylene, chlorotrifluoroethylene, and hexafluoropropylene to telomerization in an alcohol and bringing the thus obtained fluorine-containing telomer having a molecular weight of 200 to 1500 and an OH group at one of the molecular chain ends into esterification with acryloyl chloride or methacryloyl chloride.

In the second aspect of the present invention, there is provided a process for producing a novel fluorine-containing polymerizable monomer, comprising subjecting a mixture of not less than 50% by weight of vinylidene fluoride and at least one compound selected from the group consisting of vinyl fluoride, trifluoroethylene, tetrafluoroethylene, chlorotrifluoroethylene, and hexafluoropropylene to telomerization in an alcohol and bringing a fluorine-containing telomer having a molecular weight of 200 to 1500 and an OH group at one of the molecular chain ends thereof into esterification with acryloyl chloride or methacryloyl chloride.

DETAILED DESCRIPTION OF THE INVENTION

The novel fluorine-containing monomer of the present invention has a molecular weight of 300 to 1600 and a double bond at one of the molecular chain ends thereof, and is prepared by subjecting a mixture of not less than 50% by weight of vinylidene fluoride and at least one compound selected from the group consisting of vinyl fluoride, trifluoroethylene, tetrafluoroethylene, chlorotrifluoroethylene, and hexafluoropropylene to telomerization in an alcohol and bringing the thus obtained fluorine-containing telomer having a molecular weight of 200 to 1500 and an OH group at one of the main molecular chain ends thereof into esterification with acryloyl chloride or methacryloyl chloride.

In the case where such a novel fluorine-containing monomer according to the present invention is used as the soft lining material for the dental plate, 4 to 30 parts by weight of the fluorine-containing monomer according to the present invention is added to 1 part by weight of a powdery fluorine-containing copolymer of a high molecular weight, after adding an initiator such as benzoyl peroxide and the like, the resultant mixture is well kneaded at room temperature thereby obtaining an extremely soft and rubbery material showing the plastic effect of the fluorine-containing monomer according to the present invention.

As the fluorine-containing copolymer of a high molecular weight, a copolymer of at least two compounds selected from the group consisting of vinylidene fluoride, vinyl fluoride, trifluoroethylene, chlorotrifluoroethylene, tetrafluoroethylene and hexafluoropropylene, preferably a copolymer of vinylidene fluoride and one or two compounds selected from the group consisting of vinyl fluoride, trifluoroethylene, chlorotrifluoroethylene, tetrafluoroethylene and hexafluoropropylene, showing a modulus of rigidity of 10 to 150 kg/cm$^2$ may be used. Further, the most preferred fluorine-containing copolymer used in the present invention is a copolymer of 40 to 60 parts by weight of vinylidene fluoride and 20 to 30 parts by weight of each of two compounds selected from the group consisting of tetrafluoroethylene, chlorotrifluoroethylene and hexafluoroethylene.

For preparing a dental plate by using the thus obtained rubbery material, a suitable amount of the rubbery material is placed on a prepolymer of acrylic resin which has been molded by the gypsum while pulling the rubbery material with fingers or a doctor knife, and the fluorine-containing monomer contained in the rubbery material and the prepolymer are polymerized and solidified.

Then, the thus obtained soft rubbery polymer as the lining material for the dental plate shows a modulus of rigidity of 5 to 50 kg/cm$^2$, a strength of adhesion of 40 to 100 kg/cm$^2$ (fracture of a specimen occurs) and a water absorption of less than 0.2%.

The above-mentioned method for preparing a dental plate is extremely simple as compared to the conventional method for lining the dental plate in which a sheet-like fluorine-containing polymer is preliminarily heated and preliminarily molded and then it is adhered to the prepolymer of acrylic resin by a pressure. In addition, the compatibility of the thus prepared dental plate lined with the soft rubbery polymer formed from the fluorine-containing monomer according to the present invention and the powdery fluorine-containing copolymer to the mucous membrane is excellent, that is, the suction of the dental plate and the alveolar arch is excellent and no unpleasant feeling is given to the person using the dental plate and accordingly, the method is truly an epoch-making method which has been at the first time attained by using the novel fluorine-containing monomer according to the present invention.

The above-mentioned example of applying the fluorine-containing monomer according to the present invention is one example of applications thereof, and the novel fluorine-containing monomer according to the present invention has other excellent uses than that. For instance, the novel fluorine-containing monomer according to the present invention may be used in coating with paint, in which the weather-proofness, one of the excellent properties of fluorine-containing polymer, is utilized skillfully. For preparing such a coating, there are various methods, for instance, after coating a mixture of a paint with a fluorine-containing monomer added with a polymerization initiator, the thus coated monomer contained in the mixture is polymerized to be hardened, or after coating the paste-like fluorine-containing monomer onto a plastic film which is questionable in weather-proofness, the monomer is polymerized to obtain a multi-layered film which is excellent in weather-proofness.

The fluorine-containing monomer having a double bond at one of the molecular chain ends thereof and showing the above-mentioned excellent properties according to the present invention is easily available by the steps of (1) subjecting a mixture of not less than 50% by weight of vinylidene fluoride and at least one compound selected from the group consisting of vinyl fluoride, trifluoroethylene, tetrafluoroethylene, chlorotrifluoroethylene, and hexafluoropropylene to telomerization in an alcohol, thereby obtaining a fluorine-containing telomer having an OH group at one of the molecular chain ends thereof and (2) after dissolving the thus obtained telomer in a solvent such as carbon tetrachloride, chloroform and the like, adding acryloyl chloride or methacryloyl chloride drop by drop to the thus prepared solution, thereby esterifying the telomer.

The thus obtained novel fluorine-containing monomer is represented by the following general formula,

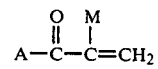

wherein A is a residual group formed by removing H from OH of the telomer and M is a hydrogen atom or methyl group.

In order to produce the lining material having the sufficient properties for the dental plate, it is necessary to mix a fluorine-containing copolymer with the fluorine-containing monomer according to the present invention having one carbon-carbon double bond at one of the main molecular chain ends thereof and a molecular weight of 300 to 1600 prepared by subjecting a mixture of not less than 50% by weight of vinylidene fluoride and at least one compound selected from the group consisting of trifluoroethylene, tetrafluoroethylene, chlorotrifluoroethylene, and hexafluoropropylene to telomerization in an alcohol and bringing the thus obtained fluorine-containing telomer into esterification with acryloyl chloride or methacryloyl chloride.

As the alcohols of the telogen in the telomerization, the primary alcohols such as methanol, ethanol and n-propyl alcohol, secondery alcohols such as isopropyl alcohol and tertiary alcohols such as tert-butyl alcohol may be used.

The lining material formed by mixing the fluorine-containing monomer with the fluorine-containing copolymer of a high molecular weight shows more excellent properties.

The molecular weight of the telomer formed by telomerization is 200 to 1500, preferably 800 to 1200, because in the case where the molecular weight of the telomer is over 1500, the molecular weight of the fluorine-containing monomer prepared from the telomer becomes more than 1600, and there are demerits of such a monomer of a large molecular weight due to the difficulty in processing and shaping such a monomer.

In the telomerization the molar ratio of telogen to taxogen is important for determining the molecular weight of the telomer, and the molar ratio of telogen to taxogen is 3 to 7 in order to produce the telomer having a molecular weight 200 to 1500.

In the case where the molar ratio of telogen to taxogen is less than 3, the molecular weight of the resultant fluorine-containing telomer is high and an undersirable solid material is produced. In addition, in the case where the molar ratio of telogen to taxogen is more than 7, the yield of the fluorine-containing telomer decreases.

The telomerization may be carried out according to the following simple procedure. In an autoclave, a mixture of not less than 50% by weight of vinylidene fluoride and at least one compound selected from the group consisting of vinyl fluoride, trifluoroethylene, tetrafluoroethylene, chlorotrifluoroethylene and hexafluoropropylene is reacted in the presence of an organic peroxide such as diacyl peroxide, dialkyl peroxydicarbonate, etc., in an alcohol.

The reaction temperature of the telomerization may be selected from the range 10° to 150° C. The initial pressure of the telomerization is in the range of 15 to 30 kg/cm$^2$. The telomerization is complete in about 8 to 12 hours.

The telomerization is preferably carried out at a temperature of 40° to 50° C. under a initial pressure of 20 to 28 kg/cm$^2$ for 8 to 10 hours by using dialkyl peroxydicarbonates.

Then, the objective telomer can be separated from the resultant reaction mixture by the conventional methods as a colourless, transparent and viscous oily substance with a yield of not less than 85%.

In the case of esterification of the thus prepared fluorine-containing telomer by acryloyl chloride or mechacryloyl chloride, it is preferable to add a tertiary amine or the like for fixing the by-produced hydrogen chloride. Also, it is preferable that the molar ratio of the acryloyl chloride or methacryloyl chloride to the fluorine-containing telomer is 0.9~1.2:1, and the molar ratio of the tertiary amine to the acryloyl chloride or methacryloyl chloride is 0.9~1.2:1.

The esterification is preferably carried out at a temperature of 0° to 100° C. for 0.5 to 3 hours including the dropwise addition time.

The present invention will be more precisely explained while referring to Examples as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE 1

In a 6 l. stainless-steel autoclave, 2,370 g (74.06 mole) of methanol were added to 12 g of di-n-propyl peroxydicarbonate and the air in the autoclave was replaced by nitrogen gas. After cooling the autoclave to about −30° C. in a methanol-dry ice bath, 597 g (9.33 mole) of vinylidene fluoride, 358 g (3.07 mole) of chlorotrifluoroethylene and 239 g (2.39 mole) of tetrafluoroethylene (the weight ratio is 50:30:20 in the order) were introduced to the autoclave and then condensed. Then, the autoclave was heated to 40° C. and the reaction was continued for 8 hours under the same temperature while stirring. With the progress of reaction, the pressure of the autoclave reduced from 24 kg/cm$^2$ to 4 kg/cm$^2$.

The reaction was discontinued and then the residual gases were released. The thus obtained reaction mixture was distilled thereby recovering methanol and obtaining the transparent oily substance.

The thus obtained substance was washed with water at 90° to 100° C. in order to decompose and remove the organic peroxide. After separating the oily substance, the obtained oily substance was distilled under reduced pressure (20 mmHg) thereby obtaining 1027 g (yield: 86%) of a colourless and transparent fluorine-containing telomer having a molecular weight of 1050 and showing the viscosity of 7500 cp at 25° C.

Into a round-bottomed flask provided with a stirrer, a reflux condenser and a dropping funnel, 100 g of the thus obtained telomer, 200 g of carbon tetrachloride and 15 g of triethylamine were introduced. On the other hand in the dropping funnel, 11 g of acryloyl chloride and 50 g of carbon tetrachloride were stocked.

While keeping the temperature of a water bath in which the flask was placed at 80° C., the solution of acryloyl chloride in carbon tetrachloride was added from the dropping funnel to the solution of the telomer under agitation in the flask drop by drop in 40 min. After stirring the mixture in the flask further for 30 min, 100 ml of water was added to the flask to dissolve the precipitated triethylamine hydrochloride, and stirring was continued for 10 min.

Then, the mixture was cooled to room temperature, and after collecting the thus separated oily layer, carbon tetrachloride was completely removed from the oily layer by steam distillation and distillation at 20 mmHg to obtain 102 g of the novel fluorine-containing monomer as a viscous, colourless and transparent oily substance.

EXAMPLE 2

Polymerization of the Novel Fluorine-containing Monomer

Into each one of the glass-stoppered conical flasks of 50 ml in capacity, 30 g of the novel fluorine-containing monomer obtained in Example 1 were introduced and after adding 0.3 g of di-n-propyl peroxydicarbonate into the monomer in one of the flasks and adding 0.3 g of benzoyl peroxide and 0.3 g of dimethylaniline in the monomer in the other flask, respectively as a polymerization initiator, the flasks were left to stand at room temperature of 23° to 25° C. Two kinds of transparent and rubbery fluorine-containing polymers were formed in the respective flasks, after 3 hours of standing in the former flask and after 5 hours of standing in the second flask.

EXAMPLE 3

By the same procedures as in Example 1 except for using a monomer mixture of 720 g (11.25 mole) of vinylidene fluoride and 240 g (2.4 mole) of tetrafluoroethylene and 240 g (1.6 mole) of hexafluoropropylene (the weight ratio is 60:20:20 in the order), the pressure of the autoclave reduced from 29 kg/cm$^2$ to 4.7 kg/cm$^2$ with the progress of reaction. And by the same procedures as in Example 1, 1020 g (yield: 85%) of a colourless and transparent fluorine-containing telomer having a molecular weight of 920 and showing the viscosity of 7300 cp at 25° C. were obtained.

By the same procedures as in Example 1 except for using the thus obtained telomer of molecular weight of 920, and stocking 12 g of methacryloyl chloride and 50 g of carbon tetrachloride in the dropping funnel, 104 g of another novel fluorine-containing monomer were obtained.

EXAMPLE 4

Polymerization of the Novel Fluorine-containing Monomer

By the same procedures as in Example 2, a novel colourless, transparent and soft fluorine-containing polymer was obtained from the novel fluorine-containing monomer prepared in Example 3.

EXAMPLE 5

Measurement of the Modulus of Rigidity of Soft Rubbery Polymer

Into each 6 g of the two fluorine-containing copolymers one of which was a copolymer of vinylidene fluoride, tetrafluoroethylene and hexafluoropropylene (the weight ratio is 60:20:20 in the order) and other of which was a copolymer of vinylidene fluoride, tetrafluoroethylene and chlorotrifluoroethylene (the weight ratio is 50:20:30 in the order), each 30 g of the two fluorine-containing monomers, respectively prepared in Examples 1 and 3 was added, and after adding 0.3 g of benzoyl peroxide to each mixture, polymerization was carried out at 100° C. After 40 minutes of the reaction, 4 kinds of the soft rubbery polymers were obtained.

Then the measurement of the modulus of rigidity of the thus obtained soft rubbery polymers was carried out according to "Test of softening temperature" by Japanese Industrial Standard (JIS) K 6745, 7.5.

The result is shown in Table below.

TABLE

Modulus of Rigidity of the fluorine-containing polymers

| No. | Compositon of copolymer (parts by weight) | | Fluorine-containing monomer | Modulus of Rigidity (kg/cm$^2$) |
|---|---|---|---|---|
| 1. | $H_2C=CF_2$ | 60 | Obtained in Ex. 1 | 25.1 |
|  | $F_2C=CF_2$ | 20 | | |
|  | $CF_3CF=CF_2$ | 20 | | |
| 2. | $H_2C=CF_2$ | 60 | Obtained in Ex. 3 | 30.7 |
|  | $F_2C=CF_2$ | 20 | | |
|  | $CF_3CF=CF_2$ | 20 | | |
| 3. | $H_2C=CF_2$ | 50 | Obtained in Ex. 1 | 16.5 |
|  | $F_2C=CF_2$ | 20 | | |
|  | $ClFC=CF_2$ | 30 | | |
| 4. | $H_2C=CF_2$ | 50 | Obtained in Ex. 3 | 18.4 |
|  | $F_2C=CF_2$ | 20 | | |
|  | $ClFC=CF_2$ | 30 | | |

EXAMPLE 6

In a mortar, 100 g of the novel fluorine-containing monomer prepared in Example 1 was mixed with 20 g of the soft fluorine-containing copolymer of vinylidene fluoride, chlorotrifluoroethylene and tetrafluoroethylene (the weight ratio is 50:30:20 in the order) showing a modulus of rigidity of 65 kg/cm$^2$, and then the thus obtained mixture was heated in an incubator at 160° C.

The mixture was taken out of the incubator when the temperature thereof rose to 150° C., and was kneaded in a mortar with a pestle till a substantially homogeneous mixture was formed (about for 10 minutes), followed by cooling the resultant homogeneous mixture to room temperature. Then 10 g of a solution of 1 g of benzoyl peroxide in acetone was added from a injection syringe to the homogeneous mixture while kneading at room temperature. Then the kneaded mixture was subjected to degassing for 30 minutes under the reduced pressure not more than 20 mmHg thereby obtaining a doughy rubbery material free from acetone.

The thus obtained doughy rubbery material was shaped to a ribbon of 10 cm in length, 1.5 cm in width and 0.4 cm in thickness and then the ribbon of the doughy rubbery material was placed on the surface of a formed prepolymer of acrylic resin having been formed to be a dental plate. The doughy rubbery material was adhered to the surface of the formed prepolymer of acrylic resin by a pressure while pulling the ribbon of the rubbery material with fingers. Then, the fluorine-containing monomer contained in the ribbon of the rubbery material and the formed prepolymer of acrylic resin were polymerized at 100° C. according to a conventional method. Owing to the polymerization and solidification of the fluorine-containing monomer contained in the rubbery material and the prepolymer of acrylic resin, a dental plate lined with a soft rubbery polymer showing a modulus of rigidity of 16.5 kg/cm$^2$ was obtained.

The thus obtained dental plate lined with the soft rubbery polymer was used by a woman of 73 years-old for 2 years without any defect and it seemed to be continuously usable still longer.

What is claimed is:

1. A dental plate lining material for a dental plate having a modulus of rigidity of 5 to 50 kg/cm$^2$, a strength of adhesion of 40 to 100 kg/cm$^2$ and a water absorbtion of less than 0.2%, prepared by mixing 4 to 30 parts by weight of a fluorine-containing monomer having a molecular weight of 300 to 1600 and a carbon-carbon double bond at one of the main molecular chain ends, prepared by subjecting a mixture of not less than 50% by weight of vinylidene fluoride and at least one compound selkected from the group consisting of vinyl fluoride, trifluoroethylene, tetrafluoroethylene, chlorotrifluoroethylene and hexafluoropropylene to telomerization in an alcohol and bringing the thus obtained fluorine-containing telomer having a molecular weight of 200 to 1500 and an OH group at one of the main molecular chain ends thereof into esterification with acryloyl chloride or methacryloyl chloride, with 1 part by weight of a powdery fluorine-containing copolymer having a high molecular weight and a modulus of rigidity of 10 to 150 kg/cm$^2$ and an initiator and polymerizing the fluorine-containing monomer.

2. The dental plate lining material of claim 1, wherein the said fluorine-containing monomer having a molecular weight of 300–1600 and a carbon-carbon double bond at one of the main molecular chain ends is prepared by subjecting a mixture of vinylidene fluoride and at least two compounds selected from the group consisting of tetrafluoroethylene, chlorotrifluoroethylene and hexafluoroethylene to telomerization in an alcohol.

3. The dental plate lining material of claim 1, wherein the said esterification is carried out in carbon tetrachloride or chloroform.

4. The dental plate lining material of claim 1, wherein the said alcohol comprises methanol, ethanol, n-propyl alcohol, isopropyl alcohol or tert-butyl alcohol.

5. The dental plate lining material of claim 1, wherein the said telomer has a molecular weight of 800–1200.

6. The dental plate lining material of claim 1, wherein a molar ratio of telogen to taxogen of 3 to 7 is used in the said telomerization.

7. The dental plate lining material of claim 1, wherein the molar ratio of acryloyl chloride or methylacryloyl chloride to the said fluorine-containing telomer is about 0.9 to 1.2:1, and a tertiary amine is added in the said esterification in a molar ratio of tertiary amine to the said acryloyl chloride or methacryloyl chloride of about 0.9 to 1.2:1.

* * * * *